US009066785B2

(12) United States Patent
Tran et al.

(10) Patent No.: US 9,066,785 B2
(45) Date of Patent: Jun. 30, 2015

(54) PACKAGING SYSTEMS FOR PERCUTANEOUSLY DELIVERABLE BIOPROSTHETIC VALVES

(75) Inventors: Don Tran, Novato, CA (US); Timothy Ryan, Shorewood, MN (US); Jeffrey Allen, Santa Rosa, CA (US); Melissa Denton, Irvine, CA (US); Adam Podbelski, St. Paul, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 962 days.

(21) Appl. No.: 12/418,684

(22) Filed: Apr. 6, 2009

(65) Prior Publication Data
US 2010/0256749 A1 Oct. 7, 2010

(51) Int. Cl.
*A61F 2/24* (2006.01)
*A61F 2/00* (2006.01)
*A61F 2/958* (2013.01)
*A61F 2/95* (2013.01)

(52) U.S. Cl.
CPC .............. *A61F 2/0095* (2013.01); *A61F 2/2412* (2013.01); *A61F 2/2418* (2013.01); *A61F 2/2436* (2013.01); *A61F 2/958* (2013.01); *A61F 2002/9505* (2013.01); *A61F 2002/9522* (2013.01)

(58) Field of Classification Search
CPC ... A61F 2/0095; A61F 2/2412; A61F 2/2418; A61F 2/2436; A61F 2002/9505; A61F 2002/9522
USPC .......... 206/438; 623/1.11, 2.1, 2.11; 606/108, 606/194, 200
See application file for complete search history.

(56) References Cited

U.S. PATENT DOCUMENTS

| 4,733,665 A | 3/1988 | Palmaz |
| 4,800,882 A | 1/1989 | Gianturco |
| 4,886,062 A | 12/1989 | Wiktor |
| 5,133,732 A | 7/1992 | Wiktor |
| 5,292,331 A | 3/1994 | Boneau |
| 5,421,955 A | 6/1995 | Lau |
| 5,560,487 A | 10/1996 | Starr |

(Continued)

FOREIGN PATENT DOCUMENTS

WO WO01/24730 4/2001

OTHER PUBLICATIONS

U.S. Appl. No. 12/357,958, Bloom et al.
(Continued)

*Primary Examiner* — Ashley Fishback

(57) ABSTRACT

A packaging system is disclosed for shipping a prosthetic tissue valve in a storage solution and preparing and loading of the bioprosthetic valve onto a catheter-based delivery system. The packaging system includes a fluid tight container filled with the storage solution attached to a delivery catheter, wherein the container surrounds the prosthetic tissue valve that is in a pre-loaded position on the delivery catheter during shipment and storage. The prosthetic tissue valve may include an attachment mechanism that attaches to the delivery catheter to properly position the tissue valve for loading within the delivery catheter. In another embodiment where the prosthetic tissue valve is not attached to the delivery catheter during shipment, the attachment mechanism may interact with the prosthetic tissue valve shipping container to prevent the bioprosthetic valve from moving during shipment.

18 Claims, 6 Drawing Sheets

(56) References Cited

U.S. PATENT DOCUMENTS

| | | |
|---|---|---|
| 5,776,161 A | 7/1998 | Globerman |
| 5,935,162 A | 8/1999 | Dang |
| 6,090,127 A | 7/2000 | Globerman |
| 6,113,627 A | 9/2000 | Jang |
| 6,425,916 B1 | 7/2002 | Garrison et al. |
| 6,663,661 B2 | 12/2003 | Boneau |
| 6,730,116 B1 | 5/2004 | Wolinsky et al. |
| 7,338,520 B2 | 3/2008 | Bailey et al. |
| 7,347,869 B2 | 3/2008 | Hojeibane et al. |
| 8,652,202 B2 * | 2/2014 | Alon et al. ............ 623/2.11 |
| 2006/0178740 A1 | 8/2006 | Stacchino et al. |
| 2006/0259136 A1 | 11/2006 | Nguyen et al. |
| 2007/0061008 A1 | 3/2007 | Salahieh et al. |
| 2007/0203503 A1 | 8/2007 | Salahieh et al. |
| 2008/0228254 A1 | 9/2008 | Ryan |
| 2008/0228263 A1 | 9/2008 | Ryan |
| 2009/0054976 A1 | 2/2009 | Tuval et al. |
| 2009/0287290 A1 | 11/2009 | Macaulay et al. |

OTHER PUBLICATIONS

U.S. Appl. No. 12/358,489, Tabor et al.

* cited by examiner

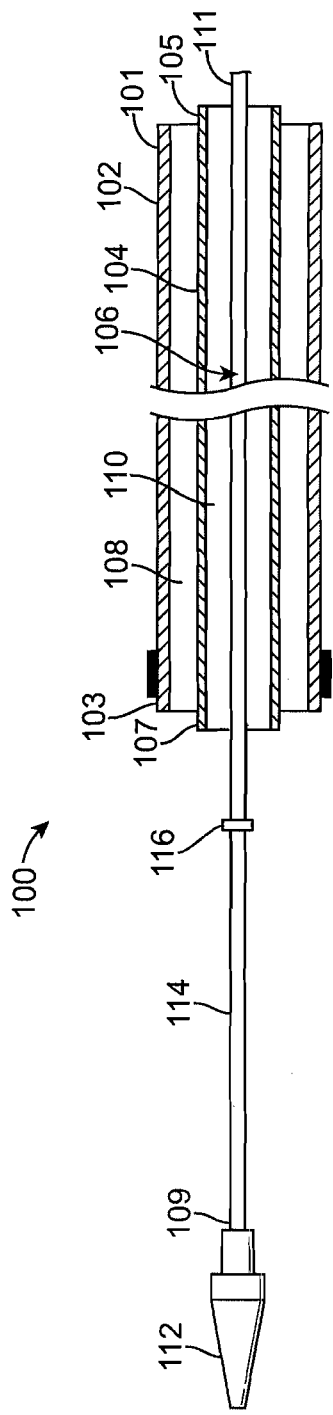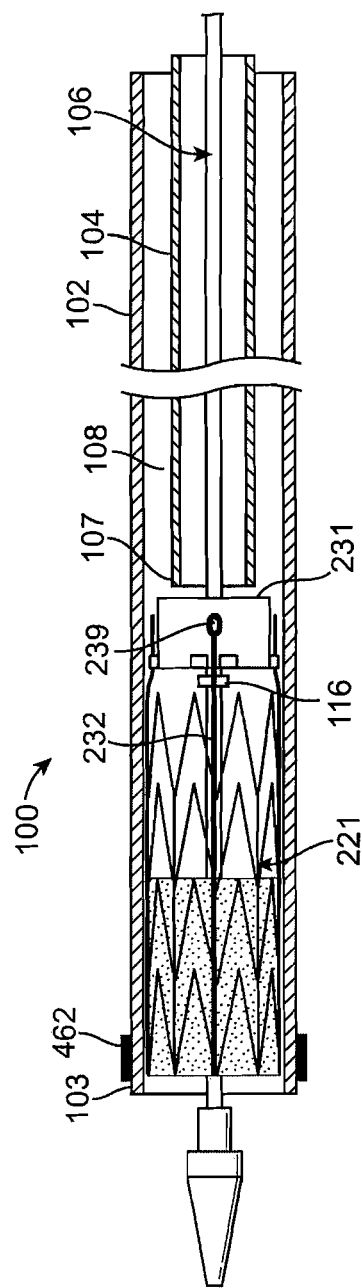

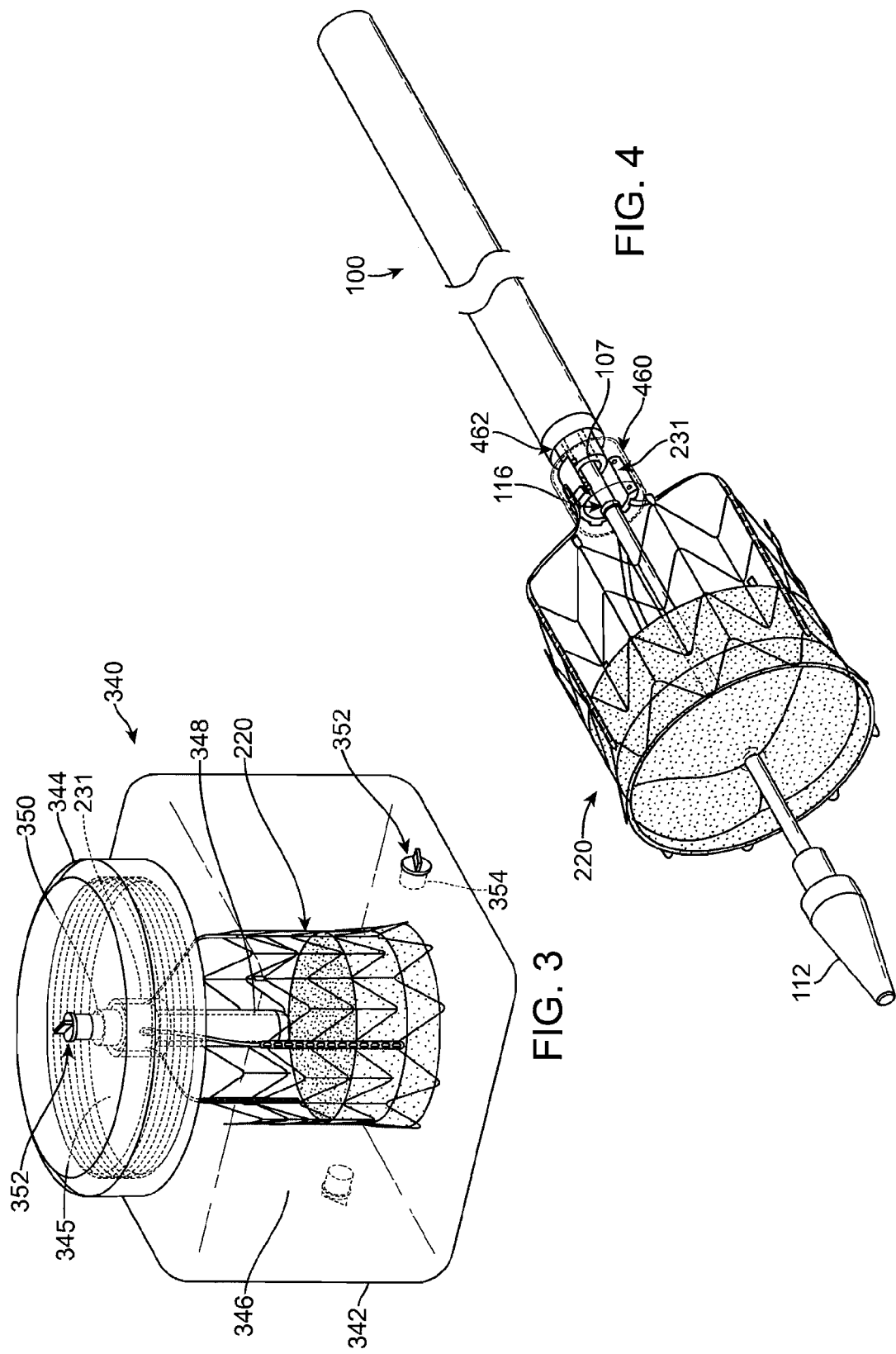

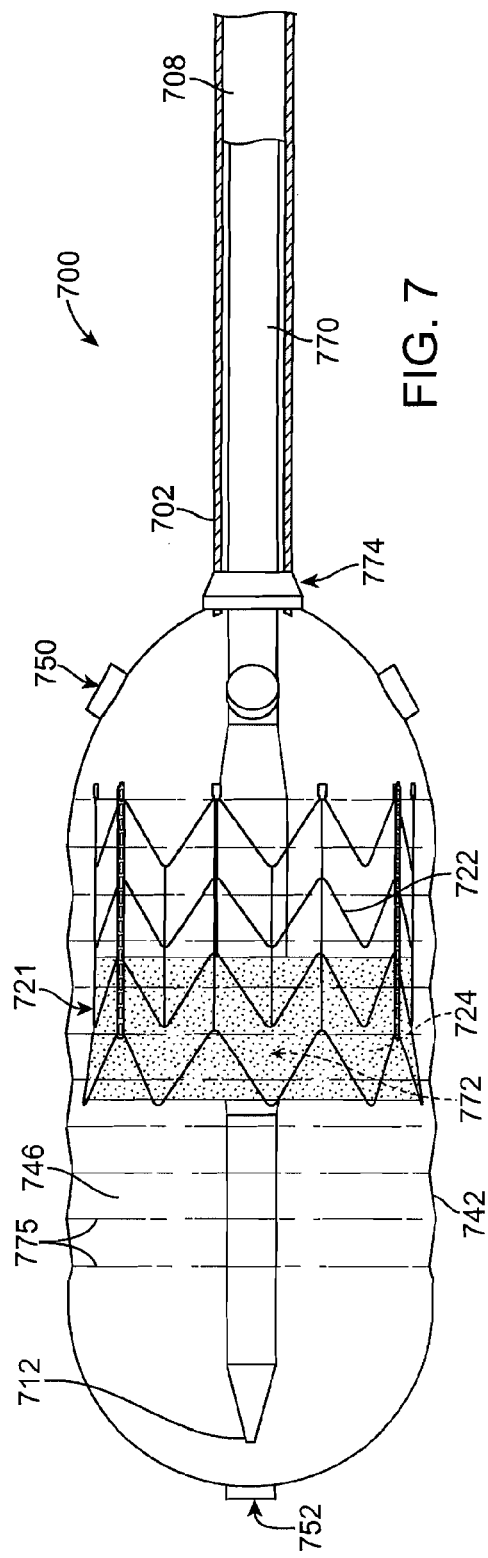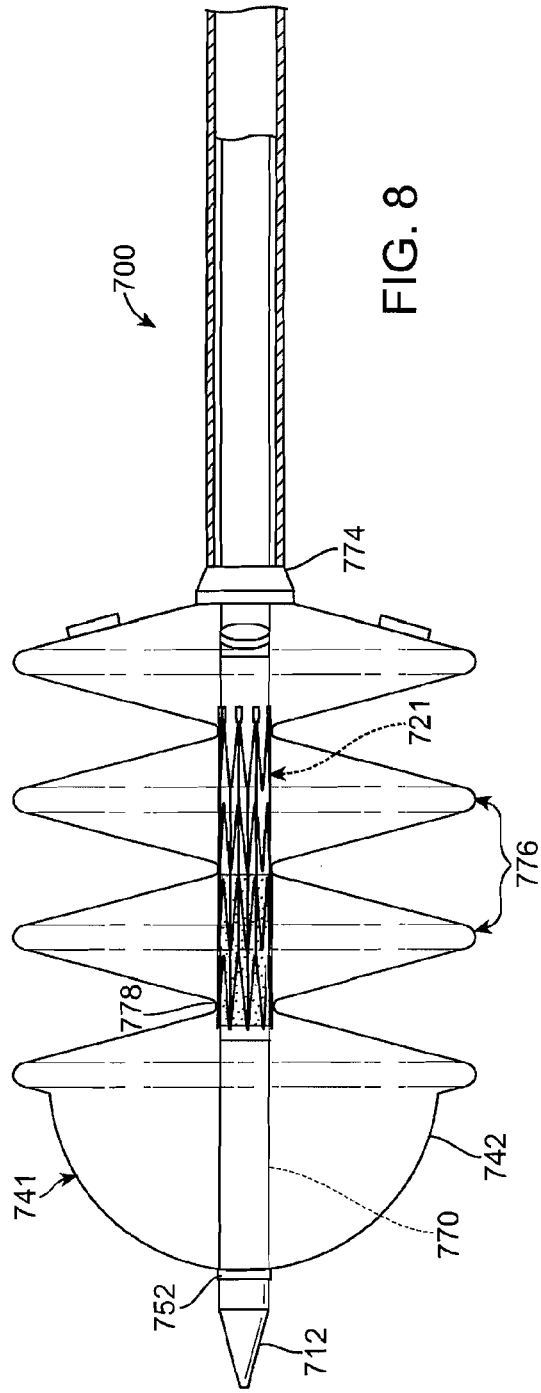

PACKAGING SYSTEMS FOR PERCUTANEOUSLY DELIVERABLE BIOPROSTHETIC VALVES

FIELD OF THE INVENTION

The invention relates generally to a packaging system for bioprosthetic valves. More specifically, the invention relates to packaging systems designed to protect a percutaneously deliverable bioprosthetic valve during shipping and/or to enable preparation and loading of the bioprosthetic valve onto a delivery catheter.

BACKGROUND OF THE INVENTION

Bioprosthetic heart valves include valve leaflets formed of flexible biological material. Bioprosthetic valves from human donors are referred to as homografts, whereas such valves from non-human animal donors are referred to as xenografts. These valves as a group are known as tissue valves. The tissue may include donor valve leaflets or other biological materials such as bovine or porcine pericardium, which are formed into the new valve structure. Depending on the method of implantation, the prosthetic valve structure may be sewn directly into place within a patient or attached to a second structure, such as a stent or other prosthesis, for implantation into a patient.

Conventional implantation of prosthetic tissue valves into the patient's body has been accomplished by invasive surgical procedures. Access to the heart valves (tricuspid, pulmonary, mitral, aortic), for instance, generally includes a thoracotomy or a sternotomy for the patient, and may include placing the patient on heart bypass to continue blood flow to vital organs, such as the brain, during the surgery. Thus, recovery from "open-heart" surgery often requires a great deal of time.

Recently percutaneous methods using catheter-based delivery mechanisms that traverse the vasculature to a treatment site have been developed allowing for minimally-invasive heart valve replacement and very short patient recovery times. Implantation of a prosthetic tissue valve percutaneously or by implantation using thoracic-microsurgery techniques is a far less invasive act than the surgical operation required for implanting traditional cardiac valve prostheses. Prosthetic tissue valves deliverable by these less invasive methods typically include an anchoring structure for supporting and fixing the valve prosthesis in the implantation position, to which the prosthetic valve leaflets are stably connected.

As mentioned above, some tissue valves are fashioned from xenografts taken from, for instance, a pig, horse, or cow, and others are fashioned from homografts taken from another human. The natural tissue for the replacement valves may be obtained from, for example, heart valves, aortic roots, aortic walls, aortic leaflets, pericardial tissue such as pericardial patches, bypass grafts, blood vessels, human umbilical tissue and the like. These natural tissues are typically soft tissues, and generally include collagen containing material. The tissue can be living tissue, decellularized tissue or recellularized tissue. The natural tissue can be fixed by crosslinking to provide mechanical stabilization, for example, by preventing enzymatic degradation of the tissue prior to implantation. A solution of glutaraldehyde or formaldehyde is typically used for fixation.

Preferably, the prosthetic tissue valves will be suspended in the glutaraldehyde storage solution until the surgical or percutaneous procedure is about to begin. As such when used in a catheter-based procedure, the clinician must prepare the fixed prosthetic tissue valve for insertion within the vasculature by removing the prosthetic tissue valve from the glutaraldehyde storage solution and rinsing the prosthetic tissue valve to remove the glutaraldehyde storage solution, followed by loading the prosthetic tissue valve onto or within the catheter-based delivery system. The clinician must take care during the preparation and loading steps not to contaminate or damage the prosthetic tissue valve. Such preparation adds time to the interventional procedure as well as risk that the tissue valve may not be properly loaded onto the catheter-based delivery system, which can lead to serious complications upon implantation of the prosthetic tissue valve at the treatment site. Due to the complexity and criticality of loading the prosthetic tissue valve onto the catheter-based delivery device, some vendors of replacement tissue valves actually provide representatives at the time of implantation to perform this aspect of the interventional procedure.

One solution to address proper loading concerns would be to "pre-load" the prosthetic tissue valve onto the catheter-based delivery system prior to shipment; however, prosthetic tissue valves heretofore have not been pre-loaded due to the sensitivity of the prosthetic tissue valves to prolonged crimping, as well as the necessity of maintaining the prosthetic tissue valve within a storage solution until just prior to implantation. Thus, there remains a need in the art for bioprosthetic valve packaging that can assure the sterility and integrity of a prosthetic tissue valve during shipment and ease loading of the prosthetic tissue valve onto a catheter-based delivery system by a clinician prior to performing the interventional procedure.

BRIEF SUMMARY OF THE INVENTION

Embodiments hereof are directed to a packaging and valve preparation system for shipping and preparing a prosthetic tissue valve having a natural tissue component in a storage solution and easing loading of the bioprosthetic valve onto a catheter-based delivery system. The packaging system includes a fluid tight shipping container or vessel filled with the storage solution, such as a glutaraldehyde solution, sealingly attached to a delivery catheter, wherein the container surrounds the prosthetic tissue valve that is in a pre-loaded position on the delivery catheter during shipment and storage. In an embodiment, the shipping container may be a bladder-type container. The prosthetic tissue valve may include an attachment mechanism that closes, crimps or otherwise attaches to the delivery catheter during shipment to properly position the bioprosthetic valve for loading within the delivery catheter by a clinician.

In another embodiment, a prosthetic tissue valve with an attachment mechanism may be unattached to the delivery catheter during shipment. In such an embodiment, the prosthetic tissue valve is disposed within a shipping container filled with a storage solution such that the attachment mechanism interacts with the shipping container to prevent the bioprosthetic valve from moving during shipment. In an embodiment, the shipping container may be a jar-like vessel with a threaded cap having a holding tube.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a cross-sectional side view of a delivery catheter according to an embodiment hereof.

FIG. 3 is a side perspective view of the prosthetic tissue valve system of FIG. 2 in a shipping container according to an embodiment hereof.

FIG. 4 is a side perspective view of the prosthetic tissue valve system of FIG. 2 being loaded onto the delivery catheter of FIG. 1.

FIG. 5 is a cross-sectional side view of the delivery catheter of FIG. 1 with the prosthetic tissue valve system of FIG. 2 in a delivery configuration.

FIG. 7 is a side view of a prosthetic tissue valve delivery system in partial section that is attached to an accordion-like shipping bladder containing the prosthetic tissue valve in a shipping/storage configuration in accordance with another embodiment hereof, wherein the bioprosthetic valve is pre-loaded onto the delivery catheter.

FIG. 8 is a side view of the delivery system and accordion-like shipping bladder of FIG. 7 with the prosthetic tissue valve collapsed for loading within the delivery catheter.

DETAILED DESCRIPTION OF THE INVENTION

Figure 2:
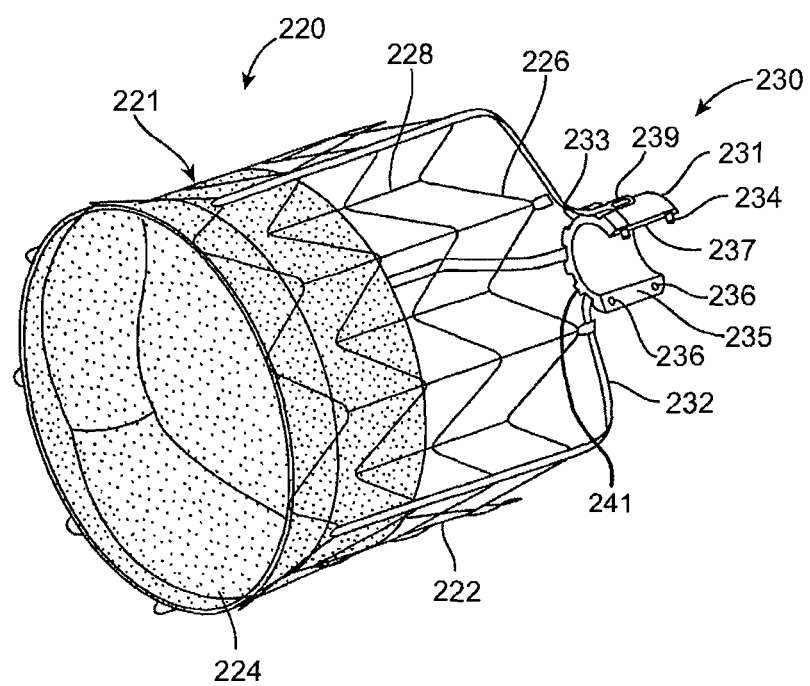
FIG. 2 is a side perspective view of a prosthetic tissue valve system according to an embodiment hereof.

Specific embodiments are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of heart valve replacement via blood vessels such as the aorta, coronary, and carotid arteries, embodiments of the present invention may also be used to deliver tissue valves in any other vessel where it is deemed useful. Furthermore, there is no intention to be bound by any expressed or implied theory presented in the preceding technical field, background, brief summary or the following detailed description.

FIG. 1 is a cross-sectional side view of a delivery catheter 100 for percutaneously delivering a prosthetic tissue valve according to an embodiment of the present invention. Delivery catheter 100 includes an outer tubular component 102, a middle tubular component 104, and an inner component 106. Outer tubular component 102 defines a first lumen 108 from a proximal end 101 to a distal end 103 thereof through which middle tubular component 104 is slidably disposed, and may alternatively be referred to as a sheath component. Middle tubular component 104 defines a second lumen 110 from a proximal end 105 to a distal end 107 thereof through which inner component 106 is slidably disposed. Inner component 106 has a proximal end 111 and distal tip 112. In the embodiment of FIG. 1, distal tip 112 is a molded polymeric piece attached to a distal end 109 of an elongate shaft portion 114 of inner component 106. In another embodiment, distal end 109 of elongate shaft portion 114 may be coiled to provide a steerable tip, such that distal tip 112 is omitted. During an interventional procedure, proximal ends 101, 105, 111 of outer tubular component 102, middle tubular component 104, and inner component 106, respectively, each extend proximally outside of the patient's body such that they may be manipulated by a clinician and one or more of proximal ends 101, 105, 111 may include a handle or knob (not shown) in order to facilitate securing a longitudinal position or sliding movement thereof.

Outer and/or middle tubular components 102, 104 may be made from polymeric tubing, such as tubing formed from, for e.g., polyethylene block amide copolymer, polyvinyl chloride, polyethylene, polyethylene terephthalate, polyamide, polyimide, polyetheretherketone (PEEK), nylon or copolymers thereof, as well as from metal tubing formed from stainless steel or nitinol, for example. In an embodiment, outer and/or middle tubular component 102, 104 may include a stainless steel hypotube, such as a hypotube of stainless steel 304 or 316, cut in a spiral or spring-like pattern to have high column strength with flexibility. In various other embodiments hereof, outer and/or middle tubular components 102, 104 may include a reinforced shaft segment, such as a shaft segment of a stainless steel braided polyimide, to provide columnar strength and pushability to delivery catheter 100 and/or multiple shaft components of varying flexibility to provide a gradual transition in flexibility as delivery catheter 100 extends distally. In another embodiment, outer and/or middle tubular components 102, 104 may be a composite shaft having an outer layer of polytetrafluoroethylene (PTFE) and an inner liner of fluorinated ethylene propylene (FEP). Inner component 106 may be a solid metallic core wire, and, in embodiments hereof, may be tapered at its distal end and/or include one or more core wire sections to provide a stiffness transition. In various other embodiments, inner component 106 may be a hollow polymeric or metallic tube that defines a guidewire lumen therethrough.

Delivery catheter 100 is depicted in FIG. 1 in a loading configuration with an annular distal stopper 116, which is attached to and surrounds inner component 106, positioned distal of distal ends 103, 107 of outer and middle tubular components 102, 104. In addition, distal tip 107 of middle tubular component 104 is positioned distal of distal end 103 of outer tubular component 102 so that middle tubular component distal end 107 acts as a proximal stopper during loading of a prosthetic valve, such as prosthetic tissue valve 220 depicted in FIG. 2 and described below. The operation of delivery catheter 100 during loading and delivery is also described in detail below. Alternatively, a proximal stopper may be attached to and surround inner component 106 an appropriate length proximal of distal stopper 116.

With reference to FIG. 2, prosthetic tissue valve system 220 includes a prosthetic tissue valve 221, having a stent-like frame 222 with valve leaflets 224 secured therein, and an attachment assembly 230. Stent-like frame 222 of prosthetic tissue valve 221 is a tubular structure having four sinusoidal rings 226 attached peak-to-peak and valley-to-valley by longitudinal connectors 228 and includes three bands 232, which may be slightly wider than longitudinal connectors 228, longitudinally extending from an outflow end of stent-like frame 222. Sinusoidal rings 226 may be attached to longitudinal connectors 228 and bands 232 by any attachment mechanism known to one of ordinary skill in the art of stent construction or may be formed pre-connected as a unitary structure, such as by laser cutting or etching the entire stent body from a hollow tube or sheet. Bands 232 may each include an eyelet 239, or in an alternate embodiment a broadened paddle-like area, at a proximal end thereof to aid in the releasable engagement of bands 232 with attachment assembly 230, as discussed in more detail below. Stent-like frame 222 is "self-expanding", which as used herein means that stent-like frame 222 has a mechanical memory to return to an expanded or deployed configuration as shown in FIG. 2. Mechanical memory may be imparted to stent-like frame 222 by thermal treatment to achieve a spring temper in stainless steel, for example, or to set a shape memory in a susceptible metal alloy, such as nitinol. As such in embodiments hereof, sinusoidal rings 226 and longitudinal connectors 228 for producing stent-like frame 222 may be made from stainless steel, a pseudo-elastic metal such as nitinol, or a nickel-based super alloy. It would be understood by one of ordinary skill in the art that other self-expanding stent-like frames, with or without tubular structures having sinusoidal rings and/or connectors, may be utilized in embodiments of the present invention without departing from the scope hereof.

Valve leaflets 224 of prosthetic tissue valve 221 may be of xenograft or homograft natural tissue and may form a bicuspid, tricuspid, or tube replacement valve. The natural tissue for the replacement valve leaflets may be obtained from, for example, heart valves, aortic roots, aortic walls, aortic leaflets, pericardial tissue, such as pericardial patches, bypass grafts, blood vessels, human umbilical tissue and the like. Valve leaflets 224 may be sutured or otherwise securely attached to stent-like frame 222 as would be known to one of ordinary skill in the art of prosthetic tissue valve construction.

Attachment assembly 230 includes a locking collar 231 and a holding sleeve 460 (shown in FIG. 4). Locking collar 231 may be formed from a flexible material, such as nylon, polyethylene, polyurethane, silicone or other suitable polymer. In the embodiment of FIG. 2, locking collar 231 is c-shaped having cog-like projections 241 surrounding a distal end thereof with a plurality of slots 233 defined between projections 241. Slots 233 are sized to provide an interference or tight fit with bands 232 of stent-like frame 222 to substantially prevent longitudinal movement between attachment assembly 230 and prosthetic tissue valve 221 with eyelets 239 being wider than slots 233 to prevent bands 232 from sliding free thereof. Locking collar 231 is surrounded by holding sleeve 460 that fits tightly enough around locking collar 231, such as in an interference fit, to prevent radial movement and/or release of bands 232 from slots 233 and thereby secures prosthetic tissue valve 221 to attachment assembly 230.

In embodiments hereof, holding sleeve 460 is a thin-walled cylinder of a polymeric or elastomeric material that is slidable or stretchable over locking collar 231. In another embodiment, holding sleeve 460 may be of a material that is heat shrinkable around locking collar 231 to radially secure bands 232 therein. In one such embodiment, holding sleeve 460 may be a short, tubular component made from a thin, stretchable material, such as silicone or polyurethane, having an inner diameter slightly larger than the diameters of catheter tip 112 and outer tubular component 102, wherein the inner diameter may be stretched to a second, larger inner diameter when holding sleeve 460 contains the unlocked or open locking collar 231, such that holding sleeve 460 substantially returns to its reduced, original inner diameter when locking collar 231 is locked or closed onto inner component 106. In an embodiment where holding sleeve 460 is formed from a non-stretchable material, while snapping or closing locking collar 231 in place a clinician may maintain a position of holding sleeve 460 over locking collar 231 to retain band(s) 232 therein until outer tubular component 102 has been distally forward to capture band(s) 232 and retain prosthetic tissue valve 221. In each of the aforementioned embodiments, holding sleeve 460 is removed after the loading of bioprosthetic valve 221 is completed.

Locking collar 231 includes projections or posts 234 protruding from a first longitudinal end surface 237 thereof that align with and have an interference fit within holes 236 in a second longitudinal end surface 235 thereof. Each post 234 is fit within a respective hole 236 when locking collar 231 is closed or crimped onto delivery catheter 100 to pre-load prosthetic tissue valve 221 thereon, as discussed in more detail below.

Figure 4A:
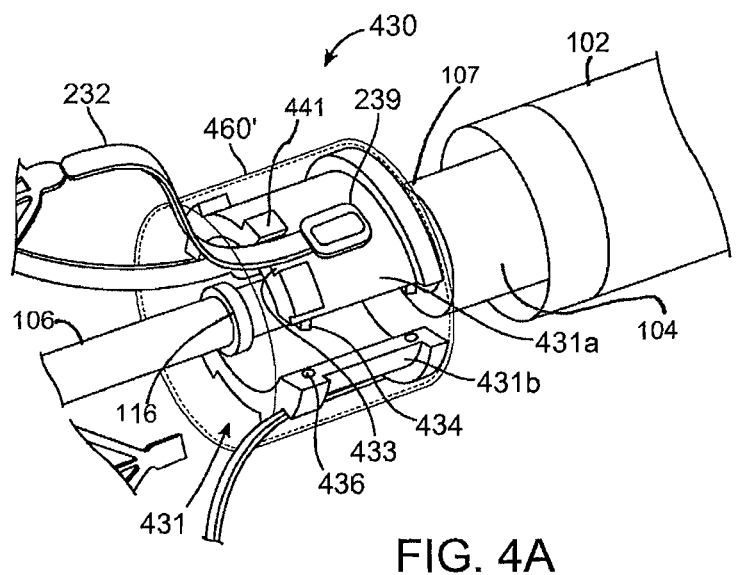
FIGS. 4A and 4B are perspective views of an attachment assembly according to another embodiment hereof.
Figure 4B:
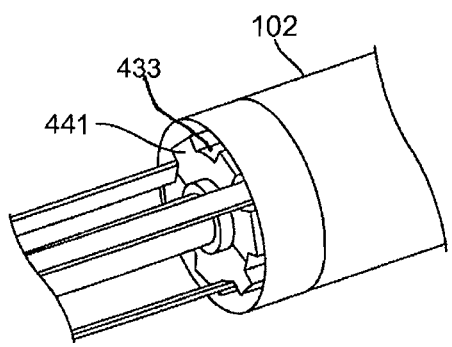

In another embodiment shown in FIGS. 4A and 4B, attachment assembly 430 includes locking collar 431 having interlocking half-ring segments 431a, 431b and holding sleeve 460'. Half-ring segment 431a includes projections or posts 434 that fit or snap within corresponding holes 436 in half-ring segment 431b. Each half-ring segment 431a, 431b includes cog-like projections 441 radially extending from a distal end thereof between which slots 433 are defined for receiving bands 232. In an embodiment, slots 433 are sized to have an interference fit with bands 232 and/or to be narrower than eyelets 239. Locking collar 431 is surrounded by holding sleeve 460', which may be a thin-walled polymeric or elastomeric cylinder/tubular component as described above with reference to the embodiments of holding sleeve 460, that radially secures bands 232 within slots 433 in a manner as previously described with reference to the embodiments of holding sleeve 460. Locking collar 431 may be formed from a flexible material, such as nylon, polyethylene, polyurethane, silicone or other suitable polymer.

In FIG. 4A, attachment assembly 430 is shown holding prosthetic tissue valve 221 in a pre-loaded configuration over inner component 106 of delivery catheter 100, with unattached half-ring segments 431a, 431b encircling inner component 106 and positioned between distal stopper 116 and distal end 107, viz., proximal stopper, of middle tubular component 104. In FIG. 4B, half-ring segments 431a, 431b have been closed or locked onto inner component 106 such that bands 232 are radially constrained within slots 433 by outer tubular component 102, which is drawn over locking collar 431 concurrent with the removal of holding sleeve 460'. With prosthetic tissue valve 221 secured in this manner to delivery catheter 100, a clinician is ready to load the bioprosthetic valve within the delivery catheter as described in more detail below.

In various other embodiments, attachment assemblies for securing prosthetic tissue valves to delivery systems in accordance herewith may include hooks, pigtails or cartridge-type connectors, such as those shown and described in patent application publications US 2008/0228254 A1 to Ryan and US 2008/0228263 A1 to Ryan, U.S. application Ser. No. 12/357,958 to Bloom et al. and/or U.S. application Ser. No. 12/358,489 to Tabor et al., each of which is incorporated by reference herein in its entirety.

FIG. 3 is a side perspective view of prosthetic tissue valve system 220 of FIG. 2 in a shipping container 340 according to an embodiment of the present invention. Shipping container 340 includes a jar-like vessel 342 having a threadably removable cap 344 for covering and uncovering a mouth 345 of vessel 342. Cap 344 has a centrally disposed holding tube 348 attached thereto that extends through locking collar 231, which is positioned within holding sleeve 460 (shown in FIG. 4), and into an interior of prosthetic tissue valve 221. With holding tube 348 so positioned, prosthetic tissue valve system 220 is prevented from moving during shipment and storage. In an embodiment, an upper or first end of the hollow holding tube 348 is accessible from an outside surface of cap 344 and defines an inflow port 350, which is fitted with a fluid-tight plug 352 during shipment and storage. Two outflow ports 354, which are apertures or holes, are shown in opposing walls of jar-like vessel 342, and are each fitted with a respective fluid-tight plug 352. Shipping container 340 holds prosthetic tissue valve 221 in a storage solution 346, such as a glutaraldehyde solution, during shipment and storage and is fluid-tight when cap 344 is threadably secured to jar-like vessel 342 and plugs 352 are in place within their respective ports 350, 354. Shipping container 340 may be made of glass or a suitable polymeric material, such as polyethylene, polyethylene terephthalate, polypropylene, acetal or nylon.

When a clinician is ready to use prosthetic tissue valve 221, plugs 352 are removed from inflow and outflow ports 350, 354 and a saline or other rinsing solution is introduced into jar-like vessel 342 via inflow port 350 to flush storage solution 346 out through outflow ports 352. As shown in FIG. 4, prosthetic tissue valve system 220 is then removed from vessel 342 and slipped/loaded over distal tip 112 of delivery catheter 100 until locking collar 231 surrounded by holding sleeve 460 is positioned around inner component shaft portion 114 between distal stopper 116 and distal end 107 of middle tubular component 104, which as mentioned above acts as a proximal stopper during loading and delivery. In FIG. 4, an optional radiopaque marker band 462 is shown surrounding distal end 103 of outer tubular component 102 to aid in fluoroscopic placement of delivery catheter 100 within a vessel. In order to secure prosthetic tissue valve system 220 to delivery catheter 100, locking collar 231 is crimped or otherwise closed down around inner component shaft portion 114 until male posts 234 are seated/snapped within holes 236, so that prosthetic tissue valve 221 is pre-loaded onto delivery catheter 100.

Once prosthetic tissue valve system 220 is properly locked onto delivery catheter 100 by snapping locking collar 231 in place, holding sleeve 460 is moved distally a short distance, for e.g., approximately 5-10 mm, to expose stent eyelets 239 and locking collar 231 while maintaining stent bands 232 in slots 233 of locking collar 231. Outer tubular component 102 is moved distally to initially capture and cover stent bands/eyelets 232, 239 and locking collar 231 with continued distal movement of outer tubular component 102, relative to middle tubular component 104 and inner component 106, collapses and loads prosthetic tissue valve system 221 into the delivery system 100. Holding sleeve 460 is removed after completion of the loading process and stent bands/eyelets 232, 239 are held within slots 233 of locking collar 231 by outer tubular component 102 so that prosthetic tissue valve 221 remains attached to locking collar 231. In FIG. 5, prosthetic tissue valve 221 is shown fully collapsed and loaded in a delivery configuration within delivery catheter 100. During loading and delivery, proximal and distal stoppers 107, 116 aid in maintaining a longitudinal position of locking collar 231, and thus prosthetic tissue valve system 220, relative to delivery catheter inner component 106. In an alternate embodiment, proximal and distal stoppers may be omitted and locking collar 231 sized to have an interference or frictional fit with inner component 106 when closed thereon.

In an embodiment hereof, delivery catheter 100 with prosthetic tissue valve 221 loaded therein may be used in a heart valve replacement procedure, wherein prosthetic tissue valve 221 is to be used to replace an insufficient/incompetent aortic valve. Loaded delivery catheter 100, as shown in FIG. 5, may be introduced into the vasculature either via a percutaneous puncture, a.k.a the Seldinger technique, or via a surgical cut-down, to be positioned at the aortic treatment site via a retrograde approach. Delivery catheter 100 may achieve access to the vasculature through a branch of the femoral artery, a carotid artery, a subclavian artery, or a brachial artery. In another embodiment, access to the heart may be attained via a transapical, transaortic and/or other minimally-invasive surgical approach. Methods and apparatus for accessing the arterial system with catheters and navigating such catheters to the level of the aortic arch are generally known in the art. Once delivery catheter 100 is positioned as desired within the native aortic valve, outer tubular component 102 is proximally retracted relative to middle tubular component 104 and inner component 106 to release prosthetic tissue valve 221 from the collapsed, delivery configuration shown in FIG. 5. When outer tubular component 102 is retracted proximal of locking collar 231, self-expanding prosthetic tissue valve 221 will expand and bands 232 will be released from locking collar 231, which remains with delivery catheter 100 for removal from the patient therewith. In its fully deployed configuration, stent-like frame 222 of prosthetic tissue valve 221 radially displaces the native aortic valve leaflets to conform and seal to the aortic annulus, as would be understood by one of ordinary skill in the art of heart or venous valve replacement.

Figure 6:
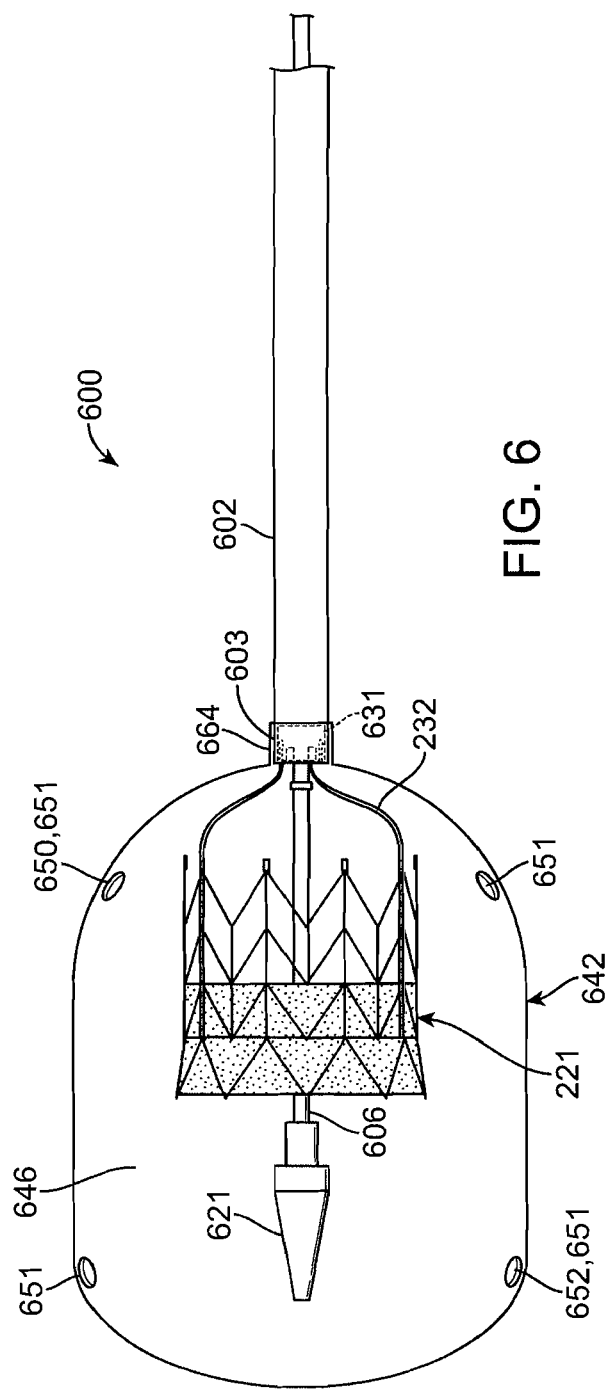
FIG. 6 is a side view of a delivery catheter attached to a shipping bladder containing the prosthetic tissue valve of FIG. 2 in a shipping/storage configuration in accordance with another embodiment hereof, wherein the bioprosthetic valve is pre-loaded onto the delivery catheter.

FIG. 6 is a side view of delivery catheter 600 attached to a shipping bladder 642 in a shipping/storage configuration in accordance with another embodiment hereof. Prosthetic tissue valve 221 is shown within shipping bladder 642 and attached/pre-loaded onto delivery catheter 600 by attachment assembly 631, which includes a collar component of metal or polymeric tubing having multiple slots around its circumference similar to slots 433 in the embodiment of FIG. 4. Attachment assembly 631 is pre-bonded onto inner tubular component 606, such that during shipment and storage the eyelet proximal ends 239 of stent bands 232 are held or "locked" in place between the collar component of attachment assembly 631 and outer tubular component 602, which is shown in FIG. 6 with a distal end positioned distal of the collar component and stent eyelets 239. In this manner, prosthetic tissue valve 221 is also maintained in a longitudinal position relative to delivery catheter 600 and shipping bladder 642. In addition, prosthetic tissue valve 221 is held in an expanded configuration within shipping bladder 642 and is not crimped or otherwise collapsed onto delivery catheter 600 during shipment, thereby preventing damage to or deformation of valve leaflets 224 that may occur during prolonged crimping. Shipping bladder 642 is a polymeric, fluid-tight vessel or sac-like container, which may or may not be distensible, with a neck portion 664 that is sealing attached around distal end 603 of outer tubular component 602 to contain storage solution 646 and prosthetic tissue valve 221 therein during shipment and storage. In order to prevent storage solution 646 from entering the guidewire lumen of delivery catheter 600, distal tip 612 is capped or otherwise sealed. In various other embodiments, shipping bladder 642 may be temporarily sealed around inner component 606 (not shown), distal tip 612 (not shown) and/or outer tubular component 602 using radial seals to prevent storage solution 646 from entering the lumens of delivery system 600. Shipping bladder 642 includes flushing ports 651, at least one of which is an inflow port 650 and at least one of which is an outflow port 652 that are weakened or thinned areas of shipping bladder 642. Shipping bladder 642 may be made of a suitable polymeric material, for e.g., polyurethane, polypropylene, polyethylene terephthalate, or nylon.

When a clinician is ready to load prosthetic tissue valve 221 within delivery catheter 600 for delivery within the patient's vasculature, flushing ports 651 are punctured so that a rinsing solution may be introduced into shipping bladder 642 via inflow port(s) 650 to flush storage solution 646 out through outflow port(s) 652. As similarly described with reference to delivery catheter 100 in the embodiment of FIGS. 4 and 5, outer tubular component 602 is advanced distally relative to inner component 606 to thereby collapse prosthetic tissue valve 221 as the prosthetic valve is drawn within outer tubular component 602, wherein in the embodiment of FIG. 6, shipping bladder 642 surrounds and protects tissue valve 221 during the loading process. In another embodiment, a series of funnels may be used to help reduce the diameter of prosthetic tissue valve 221 to aid in retracting the prosthetic valve into delivery system 600. Shipping bladder 642 is then removed so that delivery catheter 600 with prosthetic tissue valve 221 loaded in a delivery configuration therein is ready for introduction into the patient's vasculature for tracking to a treatment site. In another embodiment, prosthetic tissue valve 221 may be rinsed, shipping bladder 642 removed and then the prosthetic valve may be retracted into or otherwise covered by outer tubular component 602.

In accordance with another embodiment hereof, FIG. 7 depicts a side view of a prosthetic tissue valve delivery system 700 in partial section that is attached to an accordion-like or pleated shipping bladder 742 containing prosthetic tissue valve 721 pre-loaded thereon in a shipping/storage configuration. Prosthetic tissue valve delivery system 700 includes an elongate outer sheath 702 defining a sheath lumen 708 through which slidably extends a balloon catheter 770. Outer sheath 702 is of a similar construction as outer tubular component 102, which was previously described in detail above. Balloon catheter 770 includes a dilatation balloon 772 along a distal portion of balloon catheter 770 that is connected via an inflation lumen to a source of inflation fluid at a proximal end (not shown) of balloon catheter 770. Balloon catheter 770 is of an over-the-wire construction and as such has a full-length guidewire lumen that extends from the proximal end (not shown) to a distal tip 712 thereof. In another embodiment, balloon catheter 770 may be of a rapid exchange configuration. In various embodiments, balloon catheters manufactured and/or sold by Medtronic Inc. of Minneapolis, Minn. under the trademarks SPRINTER LEGEND, NC SPRINTER and RELIANT may be adapted for use in embodiments hereof without departing from the scope of the present invention.

Prosthetic tissue valve 721 includes stent-like frame 722 with valve leaflets 724 secured therein, which are of a similar construction as stent-like frame 222 and valve leaflets 224 described above in detail with reference to prosthetic tissue valve 221. However in the embodiment of FIGS. 7 and 8, stent-like frame 722 is balloon-expandable rather than self-expanding and as such may be constructed of, for e.g., platinum-iridium, cobalt chromium alloys (MP35N), stainless steel, tantalum or other stent materials.

Accordion-like shipping bladder 742 is a polymeric, fluid-tight vessel or container having a plurality of circumferential fold-lines or creases 775 longitudinally spaced along a length thereof that form pleats or accordion-like folds 776 when shipping bladder 742 is longitudinally compressed, as shown in FIG. 8. Shipping bladder 742 may be made of a suitable polymeric material, for e.g., polyurethane, polypropylene, polyethylene terephthalate, or nylon. Shipping bladder 742 holds prosthetic tissue valve 721 in a storage solution 746 during shipment and storage and is fluid-tight, having a neck portion (not shown) that is sealed against outer sheath 702 by a sealing ring 774, which may be of silicone, polyurethane, or a medical grade rubber. In order to prevent storage solution 746 from entering balloon catheter 770, distal tip 712 is capped or otherwise sealed. An outer surface of stent-like frame 722 of prosthetic tissue valve 721 contacts an inner surface of shipping bladder 742 by which prosthetic tissue valve 721 is held in an expanded configuration over folded balloon 772 of balloon catheter 770 and otherwise prevented from longitudinal movement during shipment and storage. Shipping bladder 742 includes proximal flushing ports 750 and distal flushing port 752, wherein flushing ports 750, 752 include Luer fittings so that at least one port or ports may be connected to a source of rinsing solution and another port or ports may be connected/directed to a fluid waste receptacle. Flushing ports 750, 752 may be weakened or thinned areas of shipping bladder 742, which are punctured for use, or may be holes/apertures in shipping bladder 742 covered by removable caps, plugs or other covering (not shown).

When a clinician is ready to load prosthetic tissue valve 721 within delivery system 700 for delivery within the patient's vasculature, one or more flushing ports 750, 752 are uncapped or punctured so that a rinsing solution may be introduced into shipping bladder 742 to flush out storage solution 746. In an embodiment, an inlet flushing port may be connected to a source of sterile saline to properly rinse prosthetic tissue valve 721, wherein the storage solution is initially evacuated from shipping bladder 742 with the sterile saline "rinsing" solution subsequently introduced. In another embodiment, a large diameter syringe or a series of syringes filled with a volume of sterile saline sufficient to replace the volume of the storage solution within shipping bladder 742 may be used to effectively rinse the prosthetic tissue valve 721. Once prosthetic tissue valve 721 is sufficiently rinsed, a distal end 741 of shipping bladder 742 is pushed or slid proximally relative to delivery system 700 to longitudinally compress shipping bladder 742 and thereby form therein accordion-like folds 776 separated by reduced-diameter compression segments or rings 778. As the overall length of shipping bladder 742 is reduced during the compression process, distal tip 712 of balloon catheter 770 exits distal flushing port 752 and compression segments 778 function to collapse/crimp prosthetic tissue valve 721 onto balloon 772 of balloon catheter 770, as shown in FIG. 8. Although compression segments 778 are shown to have a longitudinal length in the embodiment of FIG. 8, in other embodiments compression segments 778 may be merely the reduced-diameter "valley" between adjacent accordion-like folds 776. Sealing ring 774 and shipping bladder 742 are then removed and delivery system outer sheath 702 is positioned over prosthetic tissue valve 721, such that delivery system 700 with prosthetic tissue valve 721 loaded therein are in a delivery configuration ready for introduction into the patient's vasculature for tracking to a treatment site. In alternate methods of use, outer sheath 702 may be slid over collapsed tissue valve 721 or collapsed tissue valve 721 may be drawn within outer sheath 702 prior to removal of shipping bladder 742 and sealing ring 774.

In another embodiment, a balloon-expandable prosthetic tissue valve may be used with shipping bladder 642 of FIG. 6 by utilizing an external crimper such that shipping bladder 642 acts as a sterile barrier during the crimping process. Following rinsing and crimping of the prosthetic tissue valve, shipping bladder 642 is removed and the balloon-expandable prosthetic tissue valve may be loaded within the delivery system as previously discussed.

Similar to prosthetic tissue valve 221 described above, prosthetic tissue valve 721 may be percutaneously or otherwise delivered to replace an insufficient/incompetent aortic valve. However as prosthetic tissue valve 721 is balloon-expandable, once delivery system 700 is positioned as desired within the native aortic valve, outer sheath 702 is proximally retracted and dilatation balloon 772 is expanded to deploy prosthetic tissue valve 721 into apposition with the native aortic valve. Accordingly, in its fully deployed configuration, stent-like frame 722 of prosthetic tissue valve 721 radially displaces the native aortic valve leaflets to conform and seal to the aortic annulus, as would be understood by one of ordinary skill in the art of heart or venous valve replacement.

It would be understood by one of ordinary skill in the art of prosthetic valve design that known tissue valve prosthesis, such as those disclosed in U.S. Pat. No. 6,425,916 to Garrison et al., U.S. Patent Appl. Pub. No. 2006/0178740 to Stacchino et al., U.S. Patent Appl. Pub. No. 2006/0259136 to Nguyen et al., U.S. Pat. No. 7,338,520 to Bailey et al., and U.S. Pat. No. 7,347,869 to Hojeibane et al., each of which is incorporated by reference herein in its entirety, may be adapted for use in self-expanding and balloon expandable embodiments hereof without departing from the scope of the present invention. It will also be appreciated by one of ordinary skill in the art that the stent structures shown in the preceding embodiments are merely exemplary in nature and that either self-expanding or balloon-expandable stents of various forms may be adapted for use in accordance with the teaching hereof. Some examples of stent configurations that are suitable for use in embodiments hereof are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,776,161 to Globerman, U.S. Pat. No. 5,935,162 to Dang, U.S. Pat. No. 6,090,127 to Globerman, U.S. Pat. No. 6,113,627 to Jang, U.S. Pat. No. 6,663,661 to Boneau, and U.S. Pat. No. 6,730,116 to Wolinsky et al., each of which is incorporated by reference herein in its entirety.

Additionally it would be understood by one of ordinary skill in the art of medical device packaging that during shipment to the clinician, shipping container 340 and delivery catheter 100, as shown in FIGS. 1 and 3, and the delivery systems shown in FIGS. 6 and 7 would be enclosed within a suitable sterile protective packaging. In another embodiment, the protective packaging with the delivery systems therein may include insulation or be positioned within separate insulative packaging to prevent exposure of the prosthetic valve to extreme temperatures. In addition, temperature alert sensors may be incorporated into the protective packaging to ensure that a prosthetic valve damaged by exposure to extreme temperatures during shipment/storage is not used in an interventional procedure. In another embodiment, the protective packaging may include temperature sensors and/or thermal masses to protect the prosthetic valve by stabilizing its temperature when exposed during shipment/storage to extreme ambient temperatures.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A packaging and loading system for a medical device, the system comprising:
 a shipping container having a removable cap for selectively covering a mouth of the shipping container, wherein the removable cap has a holding tube attached thereto such that the holding tube of the removable cap extends into the shipping container when the removable cap is secured to the shipping container;
 a prosthetic tissue valve disposed within the shipping container, the prosthetic tissue valve having a stent-like frame with at least two bands longitudinally extending therefrom; and
 an attachment assembly fully disposed within the shipping container, the attachment assembly being releasably secured to the at least two bands of the prosthetic tissue valve to be removed from the shipping container with the prosthetic tissue valve, the attachment assembly being configured to secure the prosthetic tissue valve to a delivery catheter after the prosthetic tissue valve is removed from the shipping container, wherein when the removable cap is secured to the shipping container the holding tube of the removable cap is positioned to extend through within the attachment assembly and at least a portion of the prosthetic tissue valve to prevent movement of the prosthetic tissue valve within the shipping container; and
 a storage solution contained within the shipping container to preserve the prosthetic tissue valve.

2. The system of claim 1, wherein the shipping container is a jar-like vessel to which the cap is threadably secured.

3. The system of claim 1, further comprising:
 an inflow port for introducing a rinsing solution into the shipping container; and
 an outflow port for draining the storage and rinsing solutions from the shipping container.

4. The system of claim 3, wherein an open end of the holding tube is accessible from an outside surface of the cap and forms the inflow port and one or more apertures in the shipping container form outflow ports.

5. The system of claim 1, wherein the attachment assembly includes a locking collar and a holding sleeve surrounding the locking collar between which a portion of the at least two bands of the prosthetic tissue valve are radially secured.

6. The system of claim 5, further comprising:
 a delivery catheter having an elongate inner component slidably disposed therethrough, wherein when the attachment assembly and prosthetic tissue valve are removed from the shipping container the locking collar is sized to close around the inner component to releasably attach the prosthetic tissue valve to the delivery catheter.

7. The system of claim 6, wherein the delivery catheter includes an outer tubular component within which the inner component is slidably disposed such that relative longitudinal movement between the inner component and the outer tubular component collapses and loads the attached prosthetic tissue valve and draws the locking collar within the outer tubular component.

8. The system of claim 6, wherein the locking collar is held between proximal and distal stoppers of the delivery catheter to maintain a longitudinal position of the prosthetic tissue valve relative to the inner component.

9. A system for loading a prosthetic valve within a delivery catheter, the system comprising:
 a delivery catheter having an inner component;

a prosthetic valve having a stent-like frame, wherein at least one longitudinal band extends from the stent-like frame; and an attachment assembly independent of the delivery catheter, the attachment assembly including a collar component surrounded by a holding sleeve, wherein the longitudinal band of the stent-like frame is radially secured between the collar component and the holding sleeve such that the prosthetic valve is releasably secured to the attachment assembly prior to being attached to and loaded within the delivery catheter, wherein the collar component is configured to lock onto the inner component of the delivery catheter for attaching the prosthetic valve thereto, wherein the collar component includes cog-like projections radially extending from an outer surface thereof with a slot defined between adjacent projections in which the longitudinal band of the stent-like frame is radially secured by the holding sleeve, and wherein the collar component has a c-shaped configuration that is sized to close around the inner component of the delivery catheter to position the prosthetic valve for loading within the delivery catheter.

10. The system of claim 9, wherein the slot is sized to have an interference fit with the longitudinal band.

11. The system of claim 9, wherein the longitudinal band includes a wide proximal end that is disposed proximal of the slot and the slot is sized to be narrower than the proximal end.

12. The system of claim 9, wherein a post on a first longitudinal end surface of the c-shaped collar component fits within a hole in a corresponding second longitudinal end surface of the c-shaped collar component to lock the collar component in a closed configuration.

13. A method of using the system according to claim 9 comprising:

closing the collar component around the inner component of the delivery catheter to releasably secure the prosthetic valve to the delivery catheter; and manipulating an outer tubular component of the delivery catheter over the prosthetic valve thereby loading the prosthetic valve within the delivery catheter.

14. The method of claim 13, further comprising:

removing the holding sleeve from the collar component prior to loading the prosthetic valve within the delivery catheter.

15. The system of claim 9, wherein the collar component has an outer diameter that is sized to be slidably received within the delivery catheter when the prosthetic valve is loaded within the delivery catheter.

16. A system for loading a prosthetic valve within a delivery catheter, the system comprising:

a delivery catheter having an inner component;

a prosthetic valve having a stent-like frame, wherein at least one longitudinal band extends from the stent-like frame; and an attachment assembly independent of the delivery catheter, the attachment assembly including a collar component surrounded by a holding sleeve, wherein the longitudinal band of the stent-like frame is radially secured between the collar component and the holding sleeve such that the prosthetic valve is releasably secured to the attachment assembly prior to being attached to and loaded within the delivery catheter, wherein the collar component is configured to lock onto the inner component of the delivery catheter for attaching the prosthetic valve thereto, wherein the collar component includes coq-like protections radially extending from an outer surface thereof with a slot defined between adjacent projections in which the longitudinal band of the stent-like frame is radially secured by the holding sleeve, and wherein the collar component includes first and second half-ring segments that lock together to close around the inner component of the delivery catheter to position the prosthetic valve for loading within the delivery catheter.

17. A method of using the system according to claim 16 comprising:

closing the collar component around the inner component of the delivery catheter to releasably secure the prosthetic valve to the delivery catheter; and manipulating an outer tubular component of the delivery catheter over the prosthetic valve thereby loading the prosthetic valve within the delivery catheter.

18. The method of claim 17, further comprising:

removing the holding sleeve from the collar component prior to loading the prosthetic valve within the delivery catheter.

* * * * *